United States Patent
Chen et al.

(10) Patent No.: US 10,350,546 B2
(45) Date of Patent: Jul. 16, 2019

(54) FUNGI-BACTERIA COMPOSITE MICROECOLOGICS AND METHODS FOR PREPARING AND USING THE SAME

(71) Applicants: Jianmeng Chen, Hangzhou (CN); Jiade Wang, Hangzhou (CN); Zhuowei Cheng, Hangzhou (CN); Jianming Yu, Hangzhou (CN)

(72) Inventors: Jianmeng Chen, Hangzhou (CN); Jiade Wang, Hangzhou (CN); Zhuowei Cheng, Hangzhou (CN); Jianming Yu, Hangzhou (CN)

( * ) Notice: Subject to any disclaimer, the term of this patent is extended or adjusted under 35 U.S.C. 154(b) by 72 days.

(21) Appl. No.: 15/710,816

(22) Filed: Sep. 20, 2017

(65) Prior Publication Data
US 2018/0015410 A1    Jan. 18, 2018

Related U.S. Application Data

(62) Division of application No. 14/667,712, filed on Mar. 25, 2015, now abandoned.

(30) Foreign Application Priority Data

Dec. 24, 2014 (CN) .......................... 2014 1 0813739

(51) Int. Cl.
*B01D 53/85* (2006.01)
*C12N 1/14* (2006.01)
*C12N 1/20* (2006.01)

(52) U.S. Cl.
CPC .............. *B01D 53/85* (2013.01); *C12N 1/14* (2013.01); *C12N 1/20* (2013.01); *B01D 2251/95* (2013.01);
(Continued)

(58) Field of Classification Search
CPC .............. B01D 53/85; B01D 2251/95; B01D 2257/2064; B01D 2257/7027;
(Continued)

(56) References Cited

U.S. PATENT DOCUMENTS

| | | | | |
|---|---|---|---|---|
| 6,156,203 A | * | 12/2000 | Anthony | B01D 53/70 210/611 |
| 2002/0061270 A1 | * | 5/2002 | Osborne | B01D 53/60 423/210 |
| 2013/0196420 A1 | * | 8/2013 | Mathis | A62D 3/02 435/252.5 |

FOREIGN PATENT DOCUMENTS

| | | | |
|---|---|---|---|
| CN | 102533586 A | * | 7/2012 |
| CN | 102533586 A | | 7/2012 |

(Continued)

OTHER PUBLICATIONS

Li et al. Bacterial strain typing in the genomic era. FEMS Microbiol Rev 33 (2009) 892-916. (Year: 2009).*

(Continued)

*Primary Examiner* — Sean C. Barron
(74) *Attorney, Agent, or Firm* — Gokalp Bayramoglu

(57) ABSTRACT

A method for preparing a fungi-bacteria composite microecologics, including: cultivating and conducting high-density fermentations of *Zoogloea* sp. HJ1 which has been deposited in China Center for Type Culture Collection (CCTCC) with an accession number: CCTCC NO. M2012235, *Pandoraea* sp. FLX-1 which has been deposited in CCTCC with an accession number: CCTCC NO. M2011242, and *Ophiostoma* sp. LLC which has been deposited in CCTCC with an accession number CCTCC NO. M2014531 to obtain mixed strains; cultivating, fermenting, and vacuum drying the mixed strains to yield a resulting product which is ground into a powder; cultivating and conducting high-density fermentation of *Aspergillus* sp. HD-2 which has been deposited in CCTCC with an accession number: CCTCC NO. M2014175 and *Trichoderma* sp. LW-1 which has been deposited in CCTCC with an accession number: CCTCC NO. M2014176 to yield spores; and mixing the powder and the spores.

7 Claims, 3 Drawing Sheets

Specification includes a Sequence Listing.

(52) U.S. Cl.
CPC .......... *B01D 2257/2064* (2013.01); *B01D 2257/708* (2013.01); *B01D 2257/7022* (2013.01); *B01D 2257/7027* (2013.01); *Y02A 50/2359* (2018.01)

(58) Field of Classification Search
CPC ...... B01D 2257/708; B01D 2257/7022; Y02A 50/2359
See application file for complete search history.

(56) References Cited

FOREIGN PATENT DOCUMENTS

| | | | |
|---|---|---|---|
| CN | 102839130 A | | 12/2012 |
| CN | 103451127 A | * | 12/2013 |
| CN | 103451127 A | | 12/2013 |
| CN | 104480024 A | * | 4/2015 |
| CN | 104560728 A | * | 4/2015 |

OTHER PUBLICATIONS

Wang et al. Efficient Cellulase Production from Corn Straw by Trichoderma Reesei LW1 through Solid State Fermentation Process. Ethnobotanical Leaflets: vol. 2005 : Iss. 1 , Article 7, 8 pages. Available at: https://opensiuc.lib.siu.edu/ebl/vol2005/iss1/7 (Year: 2005).*

Yaomin Jin et al., Performance optimization of the fungal biodegradation of a-pinene in gas-phase biofilter, Process Biochemistry, 2006, 1722-1728.

Shanshan Zhang, Characterization and site-directed mutagenesis of the esterases from *Alcanivorax* sp. and Aspergillus fumigatus, China Master's Theses Full-text Database, Jun. 2014.

* cited by examiner

SEQUENCE LISTING

```
<160> NUMBER OF SEQ ID NOS: 5

<210> SEQ ID NO 1
<211> LENGTH: 599
<212> TYPE: DNA
<213> ORGANISM: Trichoderma viride

<400> SEQUENCE: 1
taggtgaacc tgcggaggga tcattaccga gtttacaact cccaaaccca atgtgaacca      60
taccaaactg ttgcctcggc ggggtcacgc cccgggtgcg tcgcagcccc ggaaccaggc     120
gcccgccgga gggaccaacc aaactctttt ctgtagtccc ctcgcggacg ttatttctta     180
cagctctgag caaaaattca aaatgaatca aaactttcaa caacggatct cttggttctg     240
gcatcgatga agaacgcagc gaaatgcgat aagtaatgtg aattgcagaa ttcagtgaat     300
```

```
catcgaatct tgaacgcac attgcgcccg ccagtattct ggcgggcatg cctgtccgag    360
cgtcatttca accctcgaac ccctccgggg ggtcggcgtt ggggacctcg ggagccccta    420
agacgggatc ccggccccga atacagtgg cggtctcgcc gcagcctctc ctgcgcagta    480
gtttgcacaa ctcgcaccgg gagcgcgcg cgtccacgtc cgtaaaacac ccaacttctg    540
aaatgttgac ctcggatcag gtaggaatac ccgctgaact taagcatatc aataagcgg    599

<210> SEQ ID NO 2
<211> LENGTH: 516
<212> TYPE: DNA
<213> ORGANISM: Aspergillus fumigatus

<400> SEQUENCE: 2
cctgcggaag gatcattacc gagtgagggc cctctgggtc caacctccca cccgtgtcta     60
tcgtaccttg ttgcttcggc gggcccgccg tttcgacggc cgccggggag gccttgcgcc    120
cccgggcccg cgcccgccga agaccccaac atgaacgctg ttctgaaagt atgcagtctg    180
agttgattat cgtaatcagt taaaactttc aacaacggat ctcttggttc cggcatcgat    240
gaagaacgca gcgaaatgcg ataagtaatg tgaattgcag aattcagtga atcatcgagt    300
ctttgaacgc acattgcgcc ccctggtatt ccggggggca tgcctgtccg agcgtcattg    360
ctgccctcaa gcacggcttg tgtgttgggc cccgtcccc ctctcccggg ggacgggccc    420
gaaaggcagc ggcggcaccg cgtccggtcc tcgagcgtat ggggctttgt cacctgctct    480
gtaggcccgg ccggcgccag ccgacaccca acttta                               516

<210> SEQ ID NO 3
<211> LENGTH: 1342
<212> TYPE: DNA
<213> ORGANISM: Ophiostoma stenoceras

<400> SEQUENCE: 3
aggtataagc aattataccg cgaaactgcg aatggctcat taaatcagtt atcgtttatt     60
tgatagtacc ttactacttg gataaccgtg gtaattctag agctaataca tgctgaaaac    120
cccgacttcg gaagggatgt atttattaga ttaaaaacca atgcccttcg gggctccctg    180
gtgattcata taacttctc gaatcgcacg gccttgcgcc ggcgatggtt cattcaaatt    240
tctgccctat caacttcga cggctgggtc ttggccagcc atggtgacaa cgggtaacgg    300
agggttaggg ctcgaccccg gagaaggagc ctgagaaacg gctactacat ccaaggaagg    360
cagcaggcgc gcaaattacc caatcccgac acggggaggt agtgacaata atactgata    420 cagggctctt tgggtcttg taattggaat gagtacaatt taattccctt aacgaggaac    480
aattggaggg caagtctggt gccagcagcc gcggtaattc cagctccaat agcgtatatt    540
aaagttgttg cagttaaaaa gctcgtagtt gaaccttggg cctggctggc cggtccgcct    600
caccgcgtgc actggtccgg ccgggtcttt ccctctgggg agccgcatgc ccttcactgg    660
gtgtgtcggg gaaccaggac ttttactttg aaaaaattag agtgttcaaa gcaggcttat    720
gctcggatac attagcatgg aataatagaa taggacgtgc ggttctattt tgttggtttc    780
taggaccgcc gtaatgatta atagggacag tcggggcat cagtattcaa ttgtcagagg    840
tgaaattctt ggatttattg aagactaact actgcgaaag catttgccaa ggatgttttc    900
attaatcagg aacgaaagtt aggggatcga agacgatcag ataccgtcgt agtcttaacc    960
ataaactatg ccgactaggg atcggacgat gttatttttt gactcgttcg gcaccttaca   1020
cgaaagtaca agtttctggg ttctgggggg agtatggtcg caaggctgaa acttaaagaa   1080
```

```
aattgacgga agggcaccac caggggtgga atctgcggct taatttgact caacacgggg    1140
aaactcacca ggtccagaca cgatgaggat tgacagattg agagctcttt cttgatttcg    1200
tgggtggtgg tgcatggccg ttcttagttg gtggagtgat ttgtctgcct aatcgcgata    1260
acgaacgaga ccttaagctg ctaaatagcc cgcgttgctt tggcagcgcg ctggcttctt    1320
agagggacta tccgctcaag cc                                             1342
```

<210> SEQ ID NO 4
<211> LENGTH: 1440
<212> TYPE: DNA
<213> ORGANISM: Zoogloea resiniphila

<400> SEQUENCE: 4

```
ttggggcggc agcttttccat gcaagtcgaa cggcagcacg ggcttcggcc tggtggcgag      60
tggcgaacgg gtgagtaatg catcggaacg tacccagtcg tggggdataa cgtagcgaaa     120
gttacgctaa taccgcatac gtcctgaggg agaaagcggg ggaccgtaag gcctcgcgcg     180
attggagcgg ccgatgtcgg attagctagt tggtggggta aaggcctacc aaggcgacga     240
tccgtagcgg gtctgagagg atgatccgcc acactgggac tgagacacgg cccagactcc     300
tacgggaggc agcagtgggg aattttggac aatgggcgaa agcctgatcc agccatgccg     360
cgtgagtgaa gaaggccttc gggttgtaaa gctctttcag acggaagaa atcttctggg       420 ctaataccct ggaggatga cggtaccgta agaagaagca ccggctaact acgtgccagc      480
agccgcggta atacgtaggg tgcgagcgtt aatcggaatt actgggcgta aagcgtgcgc    540
aggcggtgat gtaagacaga tgtgaaatcc ccgggctcaa cctgggaact gcgtttgtga    600
ctgcatcact cgagtacggc agagggaggt ggaattccgc gtgtagcagt gaaatgcgta    660
gagatgcgga ggaacaccga tggcgaaggc agcctcctgg gccagtactg acgctcatgc    720
acgaaagcgt ggggagcaaa caggattaga taccctggta gtccacgccc taaacgatgt    780
caactagttg ttcggtgagg agactcattg agtaacgcag ctaacgcgtg aagttgaccg    840
cctggggagt acggccgcaa ggttaaaact caaaggaatt gacggggacc cgcacaagcg    900
gtggatgatg tggattaatt cgatgcaacg cgaaaaacct acctaccct tgacatgcca     960 ggaacttgcc agagatggct tggtgctcga agagagcct ggacacaggt gctgcatggc   1020
tgtcgtcagc tcgtgtcgtg agatgttggg ttaagtcccg caacgagcgc aacccttgtc    1080
attagttgcc atcattaagt tgggcactct aatgagactg ccggtgacaa accggaggaa    1140
ggtggggatg acgtcaagtc ctcatggccc ttatgggtag gcttcacac gtcatacaat    1200 ggtcggtaca gagggttgcc aagccgcgag gtggagccaa tcccagaaag ccgatcgtag   1260
tccggattgg agtctgcaac tcgactccat gaagtcggaa tcgctagtaa tcgcagatca   1320
gcatgctgcg gtgaatacgt tcccgggtct tgtacacacc gcccgtcaca ccatgggagt   1380
ggggtttacc agaagtaggt agcttaaccg caaggagggc gctaccacgt agctcgtccc   1440
```

<210> SEQ ID NO 5
<211> LENGTH: 1471
<212> TYPE: DNA
<213> ORGANISM: Pandoraea pnomenusa

<400> SEQUENCE: 5

```
cgccgtggcg gctgccatta acatgcagtc gaacggcagc acgggtgctt gcacctggtg     60
gcgagtggcg aacgggtgag taatacatcg gaacgtacct tgtagtgggg gatagctcgg    120
cgaaagccgg attaataccg catacgctct gaggaggaaa gcggggggacc ttcgggcctc    180
```

-continued

```
gcgctacaag agcggccgat gtcagattag ctagttggtg aggtaaaagc tcaccaaggc    240
gacgatctgt agctggtctg agaggacgac cagccacact gggactgaga cacggcccag    300
actcctacgg gaggcagcag tggggaattt tggacaatgg gcgaaagcct gatccagcaa    360
tgccgcgtgt gtgaagaagg ccttcgggtt gtaaagcact tttgtccgga aagaaatcct    420
ctgggttaat acctcggggg gatgacggta ccggaagaat aagcaccggc taactacgtg    480
ccagcagccg cggtaatacg tagggtgcaa gcgttaatcg gaattactgg gcgtaaagcg    540
tgcgcaggcg gttttgtaag acggatgtga aatccccggg cttaacctgg gaactgcatt    600
cgtgactgca aggctagagt atggcagagg ggggtagaat tccacgtgta gcagtgaaat    660
gcgtagagat gtggaggaat accgatggcg aaggcagccc cctgggccaa tactgacgct    720
catgcacgaa agcgtgggga gcaaacagga ttagataccc tggtagtcca cgccctaaac    780
gatgtcaact agttgttggg gattcatttc cttagtaacg tagctaacgc gtgaagttga    840
ccgcctgggg agtacggtcg caagattaaa actcaaagga attgacgggg acccgcacaa    900
gcggtggatg atgtggatta attcgatgca acgcgaaaaa ccttacctac ccttgacatg    960
tacggaatcc tgctgagagg tgggagtgct cgaaagagaa ccgtaacaca ggtgctgcat   1020
ggctgtcgtc agctcgtgtc gtgagatgtt gggttaagtc ccgcaacgag cgcaaccctt   1080
gtccttagtt gctacgcaag agcactctaa ggagactgcc ggtgacaaac cggaggaagg   1140
tggggatgac gtcaagtcct catggccctt atgggtaggg cttcacacgt catacaatgg   1200
tcggtacaga gggctgccaa accgcgaggt ggagctaacc ccagaaaacc gatcgtagtc   1260
cggatcgcag tctgcaactc gactgcgtga agctggaatc gctagtaatc gcggatcagc   1320
atgtcgcggt gaatacgttc ccgggtcttg tacacaccgc ccgtcacacc atgggagtgg   1380
gttttgccag aagtaggtag cctaaccgca aggagggtgc ttaccacggc aggattcatg   1440
actgggggaa gtcgaatcaa gtgtctgcca c                                  1471
```

FUNGI-BACTERIA COMPOSITE MICROECOLOGICS AND METHODS FOR PREPARING AND USING THE SAME

CROSS-REFERENCE TO RELATED APPLICATIONS

This application is a divisional of U.S. application Ser. No. 14/667,712, filed on Mar. 25, 2015, now pending, which claims foreign priority to Chinese Patent Application No. 201410813739.4 filed Dec. 24, 2014. The contents of all of the aforementioned applications, including any intervening amendments thereto are incorporated herein by reference.

BACKGROUND OF THE INVENTION

Field of the Invention

The invention relates to a fungi-bacteria composite microecologics and methods for preparing and using the same.

Description of the Related Art

A typical process for treating organic waste gas by a fungi-bacteria composite biological system adopts gas feeding at high concentration and low flow rate and domestication by circulating fluid at a low flow rate. However, as the fungi-bacteria composite biological system is gradually formed in the domestication process, components and contents of the fungi-bacteria system are different subject to treating conditions, and the formed biological system cannot be reused or commercialized.

A typical composite microecologics includes: *bacillus, pseudomonas, alcaligenes, aspergillus*, and yeast. The composite microecologics is adapted to treat a high concentrated organic wastewater including toxic ingredients having large molecular and being difficult to be degraded and a high ammonia wastewater. However, the selection of strains is blind, and the strain source is indefinite. The conventional preparation process of the fungi-bacteria composite microecologics neglects differences in cultivation systems and pH values of the fungi and the bacteria. The composite microecologics are formed by mechanically mixing the separate solid state fermentation substances of the fungi and the bacteria. Actually, the composite microecologics has small number of live fungi/bacteria and activities thereof are not high.

SUMMARY OF THE INVENTION

In view of the above-described problems, it is one objective of the invention to provide a fungi-bacteria composite microecologics, a method for preparing the same, and a method for applying the same. The fungi-bacteria composite microecologics has simple preparation process, low preparation cost, convenient use, small volume for transportation whereby realizing industrialization, and is adapted to keep activity after long time storage.

To achieve the above objective, in accordance with one embodiment of the invention, there is provided a fungi-bacteria composite microecologics. The fungi-bacteria composite microecologics comprises the following fungus and bacterium species that have been deposited in China Center for Type Culture Collection (CCTCC) under the Budapest Treaty and that have been made available to the public: ester-degrading fungi comprising *Trichoderma viride* strain LW-1 which has been deposited in CCTCC with an accession number: CCTCC NO. M2014176 and has a DNA sequence represented by SEQ. ID. NO. 1 and *Aspergillus fumigatus* strain HD-2 which has been deposited in CCTCC with an accession number: CCTCC NO. M2014175 and has a DNA sequence represented by SEQ. ID. NO. 2; an alkene-degrading fungus comprising *Ophiostoma stenoceras* strain LLC which has been deposited in CCTCC with an accession number CCTCC NO. M2014531 and has a DNA sequence represented by SEQ. ID. NO. 3; a BTEX-degrading bacterium comprising *Zoogloea resiniphila* strain HJ1 which has been deposited in CCTCC with an accession number: CCTCC NO. M2012235 and has a DNA sequence represented by SEQ. ID. NO. 4; and a chlorinated hydrocarbon-degrading bacterium comprising *Pandoraea pnomenusa* strain FLX-1 which has been deposited in CCTCC with an accession number: CCTCC NO. M2011242 and has a DNA sequence represented by SEQ. ID. NO. 5. Both *Zoogloea resiniphila* strain HJ1 and *Pandoraea pnomenusa* strain FLX-1 are bacteria. *Ophiostoma stenoceras* strain LLC, *Trichoderma viride* strain LW-1, and *Aspergillus fumigatus* strain HD-2 are fungi. The above fungi/bacteria are adapted to decompose different kinds of pollutants, the strains have a broad substrate range, and the growth of microbes do not affect one another, so that the composite microecologics is capable of degrading waste gas containing a plurality of volatile organic compounds (VOCs).

In a class of this embodiment, the composite microecologics is in the form of a solid powder, and a number of live bacteria/fungi per gram of the composite microecologics reaches between $10^8$ and $10^9$. The solid powder is convenient for transportation, a large number of the microbes exist in per gram of the solid power, thereby decreasing the dosage in practical use.

In accordance with one embodiment of the invention, there is provided a method for preparing the fungi-bacteria composite microecologics, and the method comprises:

1) inoculating liquid culture media containing inorganic salts using seed culture tube slants of *Zoogloea resiniphila* strain HJ1 and *Pandoraea pnomenusa* strain FLX-1, respectively, for activation, in which, toluene and dichloromethane are provided as sole carbon sources, respectively; and conducting high-density fermentation in fermenters after activation;

2) inoculating a potato dextrose agar (PDA) culture medium using a seed culture plate of *Ophiostoma stenoceras* strain LLC for activation, conducting high-density fermentation in a fermenter, in which, α-pinene is provided as a sole carbon source;

3) mixing strains obtained from the high-density fermentations of 1) and 2), sterilizing a solid-state fermentation (SSF) culture medium, inoculating the SSF culture medium with mixed strains for solid-state fermentation, controlling a fermentation temperature of between 30 and 40° C. and a fermentation time of between 24 and 60 hrs;

4) vacuum drying a product obtained from the solid-state fermentation of 3), controlling a drying temperature at 40° C. and a drying time at between 24 and 48 hrs; and grinding a resulting product into a powder after drying;

5) inoculating PDA culture media with seed culture plates of *Aspergillus fumigatus* strain HD-2 and *Trichoderma viride* strain LW-1 for activation, respectively; inoculating an improved Czapek Dox culture plate containing butyl acetate and an improved Czapek Dox culture plate containing ethyl acetate with activated *Aspergillus fumigatus* strain HD-2 and *Trichoderma viride* strain LW-1, respectively, and acquiring a large amounts of spores respectively from the Czapek Dox culture plates after between 3 and 5 d cultivation; and 6) evenly mixing the powder obtained from 4) and the spores obtained from 5) at a weight ratio of (3-5):1, whereby obtaining a composite microecologics. In the above process, different strains are cultivated in particular cultivation systems, and the drying time and drying temperature are reasonably controlled, whereby acquisition of a large amount of strains and the activities thereof are ensured. The fungal spores and the solid state fermentation powder are mixed, so that the separate degradation activities of the fungi and the bacteria are kept to the maximum extent.

In a class of this embodiment, the liquid culture medium containing inorganic salts and culture media in the fermenters of 1) comprise: 0.376 g/L of $KH_2PO_4$, 0.456 g/L of $K_2HPO_4$, 0.48 g/L of $(NH_4)_2SO_4$, 0.68 g/L of $NaNO_3$, 0.25 g/L of $Mg(NO_3)_2$, 0.011 g/L of $CaCl_2.2H_2O$, trace elements (0.06 g/L of $MnCl_2.H_2O$, 0.088 g/L of $ZnCl_2$, 0.01 g/L of KI, 0.1 g/L of $NaMoO_4.2H_2O$, and 0.05 g/L of $H_3BO_3$, and pH values thereof are between 7.0 and 7.2. The liquid culture medium containing the inorganic salts and the culture media in the fermenters are performed with moist heat sterilization at a temperature of 121° C. for between 30 and 40 min. Toluene and dichloromethane are supplied for *Zoogloea resiniphila* strain HJ1 and *Pandoraea pnomenusa* strain FLX-1 as the carbon sources in activation and high-density fermentation, respectively. Temperatures for the activation and fermentation cultivation of strains in 1) are controlled at between 30 and 35° C. and dissolved oxygen contents are controlled at between 2 and 3 mg/L. The above technical parameters enable the cultivation systems and cultivation environments to be suitable for growth of the bacteria, so that a large amount of bacteria are acquired in a relatively short period.

In a class of this embodiment, the PDA culture medium in 2) comprises: 200 g/L of a potato, 20 g/L of glucose (or sucrose), and 20 g/L of an agar, and a pH value thereof is 6.5. A culture medium in the fermenter in 2) comprises: 2.0 g/L of $NH_4Cl$, 0.47 g/L of $Na_2HPO_4$, 0.45 g/L of $KH_2PO_4$, 0.5 g/L of $MgSO_4$, 0.01 g/L of anhydrous $CaCl_2$), and trace elements (0.001 g/L of $Mn^{2+}$, $Fe^{2+}$, $Cu^{2+}$, and $Zn^{2+}$, respectively), a pH value thereof is between 4.2 and 4.6, and a carbon source thereof is α-pinene. Both the PDA culture medium and the culture medium of the fermenter in 2) are performed with moist heat sterilization at a temperature of 121° C. for between 30 and 40 min. The activation and the fermentation cultivation of *Ophiostoma stenoceras* strain LLC in 2) are conducted at temperatures of between 30 and 35° C. A dissolved oxygen concentration during the fermentation cultivation is controlled at between 2 and 3 mg/L. The above technical parameters enable the cultivation systems and cultivation environments to be suitable for growth of the fungi, so that a large amount of the fungi are acquired in a relatively short period.

In a class of this embodiment, the SSF culture medium of step 3) comprises a solid state composite comprising between 45 and 50 wt. % of a wheat bran, between 25 and 30 wt. % of a sawdust, and between 25 and 30 wt. % of and a powdered activated carbon. An aqueous solution having a volume of between 1 and 2 times of that of the solid state composite is added to yield a mixture. The aqueous solution comprises: 20 g/L of a yeast extract, 20 g/L of a potato, and 5 g/L of NaCl. A pH value of the mixture is regulated to be between 6.8 and 7.2. The mixture is conducted with moist heat sterilization at a temperature of 121° C. for between 30 and 40 min and then cooled to obtain the SSF culture medium. The SSF culture medium is capable of acquiring a relative large quantity of biomass within a relatively short period, besides, a large quantity of the biomass is absorbed per unit volume.

In a class of this embodiment, an inoculum of the mixed strains in 3) is between 5 and 20%. Thus, the inoculation microbes grow well in the cultivation system.

In a class of this embodiment, in step 5), the improved Czapek Dox culture plates comprises: 3 g/L of $NaNO_3$, 0.5 g/L of $MgSO_4$, 0.5 g/L of KCl, 0.01 g/L of $FeSO_4$, and 20 g of an agar, and pH values thereof is between 6.0 and 6.5. Butyl acetate and ethyl acetate are supplied as carbon sources for *Aspergillus fumigatus* strain HD-2 and *Trichoderma viride* strain LW-1, respectively. The improved Czapek Dox culture plates are conducted with moist heat sterilization at a temperature of 121° C. for between 30 and 40 min. Thus, the cultivated microbes have relatively good degradation capability on butyl acetate and ethyl acetate.

In a class of this embodiment, the composite microecologics obtained from 6) is in a solid powder state and is adapted to maintain viabilities thereof after preservation at room temperature or a temperature of 4° C. for more than 45 d. Thus, the degradation activity of the composite microecologics is well kept.

In accordance with one embodiment of the invention, there is provided a method for treating waste gas comprising chlorinated hydrocarbons, alkenes, aromatic hydrocarbons, and esters comprising applying the fungi-bacteria composite microecologics. The fungi-bacteria composite microecologics is directly added to an inoculation sludge in a reactor. An addition of the fungi-bacteria composite microecologics in controlled to be between 0.5 and 2 kg per cubic meter of a filler. When the above composite microecologics is added, the time for initiating the reactor is obviously shortened, and the fungi and bacteria symbiotics is formed, thereby accelerating the formation of the biofilm.

Advantages according to embodiments of the invention are summarized as follows:

The composite microecologics of the invention adopts bacteria and fungi possessing particular VOCs degradation activities and is adapted to effectively overcome shortages of the conventional reactor inoculated with activated sludge. Not only is the number of the fungi/bacteria possessing high degradation activities per unit volume significantly improved and the initiating time of the reactor shortened, but also advantages of the fungi and bacteria are presented, and the composite microecologics has improved adaptability on the environment and great development potential and application prospect in engineering practice of the purification of the waste gas.

The method for preparing the fungi-bacteria composite microecologics of the invention has a simple process, low price of the raw materials. Each volume unit of the prepared composite microecologics contains a large number of live microbes and has high degradation activity. The composite microecologics is capable of recovering the degradation activity in a short period after low temperature storage and is applicable for biological purification of the industrial waste gas. A fungi-bacteria symbiotic system is formed during the application process, and separate characters of the two types of microbes are ensured.

BRIEF DESCRIPTION OF THE DRAWINGS

The invention is described hereinbelow with reference to the accompanying drawings, in which.

DETAILED DESCRIPTION OF THE EMBODIMENTS

Figure 1:
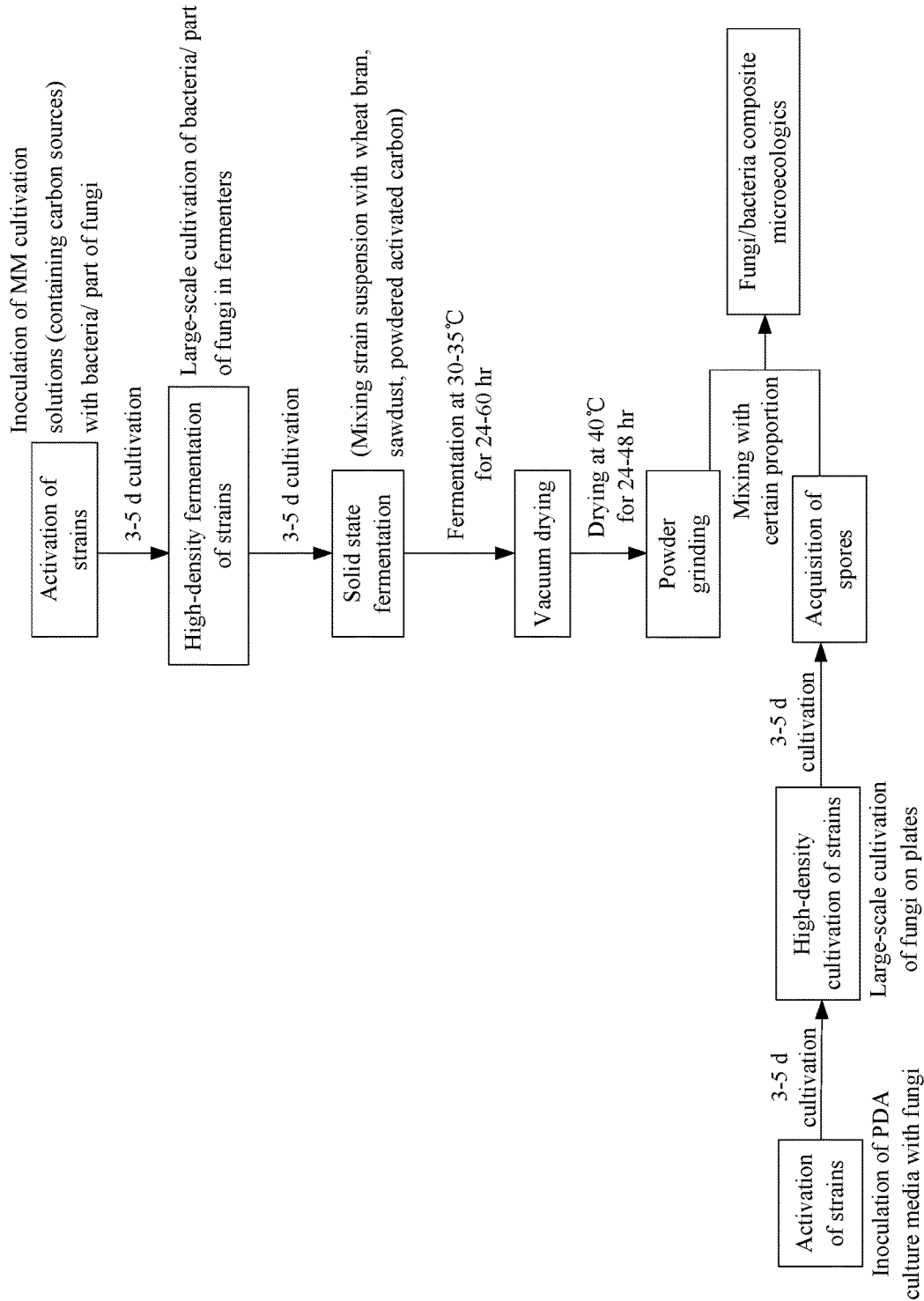
FIG. 1 is a flow chart of a method for preparing a fungi-bacteria composite microecologics according to one embodiment of the invention.

For further illustrating the invention, experiments detailing a fungi-bacteria composite microecologics and methods for preparing and using the same are described below. It should be noted that the following examples are intended to describe and not to limit the invention.

Example 1 Preparation of Fungi-Bacteria Composite Microecologics

Microbes related in the invention are all deposited in China Center for Type Culture Collection (CCTCC), Wuhan University, Wuhan, 430072, China. The microbes are as follows:

ethyl acetate-degrading fungus *Trichoderma viride* strain LW-1, accession number for the deposit: CCTCC NO. M2014176, date of the deposit: May 9, 2014;

butyl acetate-degrading fungus *Aspergillus fumigatus* strain HD-2, accession number for the deposit: CCTCC NO. M2014175, date of the deposit: May 9, 2014;

α-pinene-degrading fungus *Ophiostoma stenoceras* strain LLC, accession number for the deposit: CCTCC NO. M2014531, date of the deposit: Nov. 5, 2014;

toluene-degrading bacterium *Zoogloea resiniphila* strain HJ1, accession number for the deposit: CCTCC NO. M2012235, date of the deposit: Jun. 21, 2012, disclosed in Chinese patent application number 201310281412.2; and dichloromethane-degrading bacterium *Pandoraea pnomenusa* strain FLX-1, accession number for the deposit: CCTCC NO. M2011242, date of the deposit: Jul. 14, 2011, disclosed in Chinese patent application number 201110370070.2.

Separation, purification, and identification of *Ophiostoma stenoceras* strain LLC are as follows:

A biofilm is collected from an α-pinene-treating biofilter and placed in an culture medium containing inorganic salts for cultivation. A concentration of α-pinene is gradually increased within a range of between 50 and 200 mg/L. When the concentration of α-pinene decreases, 200 mL of a mixed solution is smeared on a solid state culture medium containing inorganic salts containing α-pinene as a sole carbon source and is continuously streaked for separation, so that a purified strain is finally obtained. The purified strain is inoculated on a slant culture medium and the slant culture medium is then stored in a refrigerator at a temperature of 4° C.

PCR amplification of a genomic DNA of the above purified strain is conducted using universal primers of internal transcribed spacer (ITS) of fungi to obtain a target DNA fragment. The sequence of the target DNA fragment is compared with genomic sequence from NCBI database, which indicates that the purified strain and the strain *Ophiostoma stenoceras* have 100% sequence homology. Clustal X2.0 and MEGA 4.0 (1000 times sampling analyses) are adopted to construct a phylogenetic tree. From genetic distance and ITS sequence comparison, the purified strain is identified as *Ophiostoma stenoceras* and is denominated as LLC.

Separation, purification, and identification of *Aspergillus fumigatus* strain HD-2 are as follows:

A sludge from a wastewater treatment plant is air-aerated for three days. 50 mL of a supernatant is then collected and centrifuged, and a deposited sludge is added to a brine bottle containing 50 mL of a liquid culture medium containing inorganic salts which is previously sterilized at a temperature of 110° C. for 40 min, and antibiotics (0.001 g of streptomycin and gentamicin) is added. After a bottle plug is inserted, 5 µL of butyl acetate (a concentration of which is approximately 88 mg/L) is added. The brine bottle is placed on a shaking table and is cultivated at a temperature of 30° C. and at a rotational speed of 160 rpm. The concentration of butyl acetate is then gradually increased. When butyl acetate is obviously degraded, 2 mL of a mixed strain solution is collected and smeared on a Czapek Dox culture medium in the absence of the carbon source. A filter paper having a diameter of 1 cm is placed on a central position of a cover of a petri dish, and 5 µL of butyl acetate is dropped on the filter paper. The mixed strain solution is continuously streaked for separation, and a purified strain is obtained. A PDA slant medium is inoculated with the purified strain and then stored in a refrigerator at a temperature of 4° C.

PCR amplification of a genomic DNA of the purified strain is conducted by universal primers of ITS of fungi to obtain a target DNA fragment. The sequence of the target DNA fragment is compared with the genomic sequence from NCBI database, which indicates that the ITS sequence of the purified strain and the ITS sequence of strain *Aspergillus fumigatus* have 100% sequence homology. Thereafter, Clustal X2.0 and MEGA 4.0 (1000 times sampling analyses) are adopted to construct the phylogenetic tree. From genetic distance and ITS sequence comparison, the purified strain is identified as *Aspergillus fumigatus*, and is denominated as HD-2.

Separation, purification and identification of *Trichoderma viride* strain LW-1 are as follows:

An activated sludge is collected from an aeration tank of a wastewater treatment plant. The activated sludge is washed by a tap water for five times and air-aerated for 48 hrs for the purpose of removing organic compound residue as much as possible. After that, an inorganic culture solution is prepared, and ethyl acetate is used as the sole carbon source for domestication of the activated sludge. The inorganic culture solution is replaced with fresh one every 3 d, and after 40 d of domestication, separation can be performed. 50 mL of a supernatant is collected from a domestication bottle and is centrifuged, a deposited sludge is then collected and added to a brine bottle containing 50 mL of a sterilized culture medium containing inorganic salts, and antibiotics are added. After that, a bottle plug is inserted, and ethyl acetate is added (a concentration of which is 50 mg/L). The brine bottle is placed on the shaking table at the temperature of 30° C. and the rotational speed of 160 rpm. The concentration of ethyl acetate is gradually increased, and when obvious degradation of ethyl acetate occurs, 2 mL of a mixed strain solution is smeared on a solid state culture medium containing inorganic salts containing ethyl acetate and continuously streaked for separation, whereby a purified strain is finally obtained. A PDA slant culture medium is inoculated with the purified strain and is stored at the refrigerator at the temperature of 4° C.

Based on the homology of ITS sequence, Clustal X2.0 and MEGA 4.0 (1000 times sampling analyses) are adopted to construct the phylogenetic tree. From genetic distance and ITS sequence comparison, the purified strain is identified as *Trichoderma viride*. It is indicated from Biolog FF microplate that the strain has a relative good conformity degree with *Trichoderma viride* SIM index within the system, which indicates that the separated strain LW-1 belongs to *Trichoderma viride*.

As shown in FIG. 1, preparation of a fungi-bacteria composite microecologics is specifically as follows:

1) Activation of Strains

Inorganic liquid media are inoculated from seed culture tube slants of *Zoogloea resiniphila* strain HJ1 and *Pandoraea pnomenusa* strain FLX-1, respectively, for activation. The liquid culture media containing inorganic salts comprise: 0.376 g/L of $KH_2PO_4$, 0.456 g/L of $K_2HPO_4$, 0.48 g/L of $(NH_4)_2SO_4$, 0.68 g/L of $NaNO_3$, 0.25 g/L of $Mg(NO_3)_2$, 0.011 g/L of $CaCl_2.2H_2O$, trace elements (0.06 g/L of $MnCl_2.H_2O$, 0.088 g/L of $ZnCl_2$, 0.01 g/L of KI, 0.1 g/L of $NaMoO_4.2H_2O$, and 0.05 g/L of $H_3BO_3$). pH values of the liquid culture media are regulated to be 7.0. Both the culture media are conducted with moister heat sterilization at a temperature of 121° C. for between 30 and 40 min. The culture media are then cooled and inoculated with the strains. *Zoogloea resiniphila* strain HJ1 and *Pandoraea pnomenusa* strain FLX-1 are supplied with toluene and dichloromethane as sole carbon sources, respectively, and cultivated on a shaking table at a temperature of 32° C. After 5 d cultivation, inoculation solutions are obtained.

PDA culture media are inoculated with seed culture plates of *Ophiostoma stenoceras* strain LLC, *Aspergillus fumigatus* strain HD-2, and *Trichoderma viride* strain LW-1, respectively, for activation. The PDA culture media comprise: 200 g/L of a potato, 20 g/L of glucose (or sucrose), and 20 g/L of an agar. pH values of the PDA culture media are regulated to be 6.5. The PDA culture media are performed with moist heat sterilization at the temperature of 121° C. for between 30 and 40 min. After the PDA culture media are cooled, the strains are respectively smeared on the solid culture medium plates and cultivated at the temperature of 32° C. Inoculums are obtained after 5 d cultivation.

2) Acquisition of Strains

The inoculation solutions of strains *Zoogloea resiniphila* strain HJ1 and *Pandoraea pnomenusa* strain FLX-1 after activation are inoculated in fermenters containing liquid culture media containing inorganic salts for conducting high-density cultivation. Toluene and dichloromethane are continuously fed as the sole carbon sources, respectively. The temperature, the pH value, and the dissolved oxygen concentration are monitored on line and are controlled at 32° C., 7.0, and between 2 and 3 mg/L, respectively. A large amount of strains are acquired after 3 d cultivation and then centrifuged for accumulation.

The activated strain *Ophiostoma stenoceras* strain LLC is inoculated in a fermenter containing a liquid culture medium containing inorganic salts for high-density fermentation. α-pinene is continuously fed into the fermenter as the carbon source. The liquid culture medium containing inorganic salts comprises: 2.0 g/L of $NH_4Cl$, 0.47 g/L of $Na_2HPO_4$, 0.45 g/L of $KH_2PO_4$, 0.5 g/L of $MgSO_4$, 0.01 g/L of anhydrous $CaCl_2$), and trace elements (0.001 g/L of $Mn^{2+}$, $Fe^{2+}$, $Cu^{2+}$, and $Zn^{2+}$, respectively). The temperature, the pH value, and the dissolved oxygen concentration are monitored on line and are controlled at 32° C., 4.4, and between 2 and 3 mg/L, respectively. A large amount of mycelia are acquired after 3 d cultivation and then centrifuged for accumulation.

The inoculation solutions of *Aspergillus fumigatus* strain HD-2 and *Trichoderma viride* strain LW-1 after activation are inoculated on improved Czapek Dox culture plates for high-density cultivation. Butyl acetate and ethyl acetate are supplied as the carbon sources, respectively. The improved Czapek Dox culture plates comprise: 3 g/L of $NaNO_3$, 0.5 g/L of $MgSO_4$, 0.5 g/L of KCl, 0.01 g/L of $FeSO_4$, and 20 g of the agar. pH values of the improved Czapek Dox culture plates are 6.0. The improved Czapek Dox culture plates are placed in an incubator for cultivation at the temperature of between 30 and 35° C. After 5 d cultivation, a large amount of spores are obtained from the plates, respectively.

3) Preparation of Composite Microecologics

Strains of *Zoogloea resiniphila* strain HJ1, *Pandoraea pnomenusa* strain FLX-1, and *Ophiostoma stenoceras* strain LLC obtained from high-density fermentation are evenly mixed and then inoculated on a SSF culture medium for solid state fermentation. The fermentation temperature is 35° C., and the fermentation time is 40 hrs. The SSF culture medium in 3) comprises a solid state composite comprising between 45 and 50 wt. % of a wheat bran, between 25 and 30 wt. % of a sawdust, and between 25 and 30 wt. % of and a powdered activated carbon. An aqueous solution having a volume of between 1 and 2 times of that of the solid state composite is added to the solid state composite to yield a mixture. The aqueous solution comprises: 20 g/L of a yeast extract, 20 g/L of a potato, and 5 g/L of NaCl. A pH value of the mixture is regulated to be between 6.8 and 7.2. The mixture is conducted with moist heat sterilization at the temperature of 121° C. for between 30 and 40 min and then cooled to obtain the SSF culture medium, which is then inoculated with a strain suspension for cultivation.

A product obtained from the solid state fermentation is vacuum dried at a drying temperature of 40° C. for 24 hrs, and is further ground to yield a powder. The powder is then mixed with spores of *Aspergillus fumigatus* strain HD-2 and *Trichoderma viride* strain LW-1 at a weight ratio of 4:1.

Example 2 Performance Measurement of the Fungi-Bacteria Composite Microecologics The constructed fungi-bacteria composite microecologics are performed with biomass and degradation activity stability tests. The method for testing the biomass is specifically conducted as follows: 1 g of composite microecologics is inoculated on a sterilized LB solid culture medium and cultivated at the temperature of 30° C. for 24 hrs, and the cell number of the bacteria is then measured; and 1 g of composite microecologics is inoculated on a sterilized PDA solid culture medium and cultivated at the temperature of 35° C. for 48 hrs, and the weight of the fungi is then measured. The measurement of the cell number of the bacteria adopts dilution smear, that is, conducting gradient dilution before counting the number of colonies. The measurement of the fungi biomass adopts dry weight method, that is, mycelia are scrapped from the PDA culture medium and dried at the temperature of 80° C. before weighing. The LB solid culture medium comprises: 10 g/L of a tryptone, 5 g/L of a yeast extract, 10 g/L of NaCl, and 15 g/L of the agar, and a pH value of the LB solid culture medium is 7.2. The PDA culture medium comprises: 200 g/L of a potato, 20 g/L of glucose (or sucrose), and 20 g/L of the agar, and a pH value thereof is 6.5.

It is indicated from the results that the number of effective live colonies on the LB plate (diluted to $10^{-6}$) after 24 hrs cultivation is 298; and the number of the effective live colonies on the LB plate (diluted to $10^{-7}$) after 48 hrs is 31. After conversion, the composite microecologics contains $6.08 \times 10^8$ live bacteria per gram of a dried composite microecologics. An effective weight increase of the PDA plate is 0.057 g after 24 hrs cultivation and 0.248 g after 48 hrs cultivation. After conversion, the composite microecologics contains 0.4296 g of fungi per gram of the dried composite microecologics.

The degradation activity stability test is conducted as follows: 2 g of the fungi-bacteria composite microecologics after 0 h, 1 d, 5 d, 15 d, 30 d, and 45 d storage in the 4° C. refrigerator are inoculated to sterilized liquid culture media containing inorganic salts, respectively. The liquid culture media are added with α-pinene, ethyl acetate, butyl acetate, toluene, and dichloromethane to enable concentrations thereof reach 50 mg/L respectively. After that, the culture media are sealed and shaking cultivated, and removal efficiencies of each pollutant are measured after 48 hrs and 72 hrs, respectively.

Figure 2A:
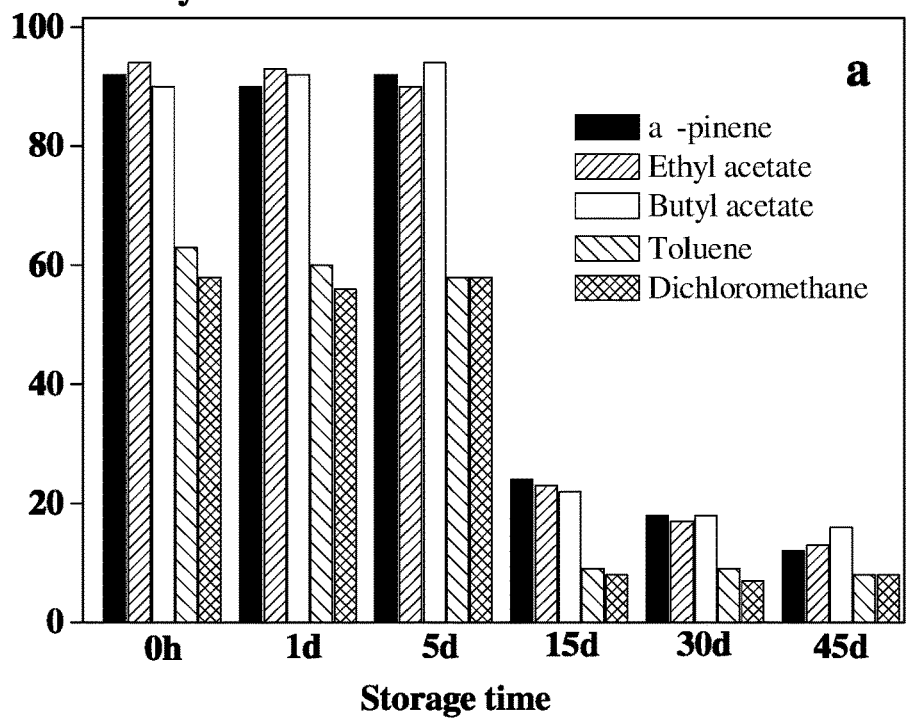
FIG. 2A shows a test result of degradation activity stability of a fungi-bacteria composite microecologics after 48 hrs cultivation according to one embodiment of the invention.
Figure 2B:
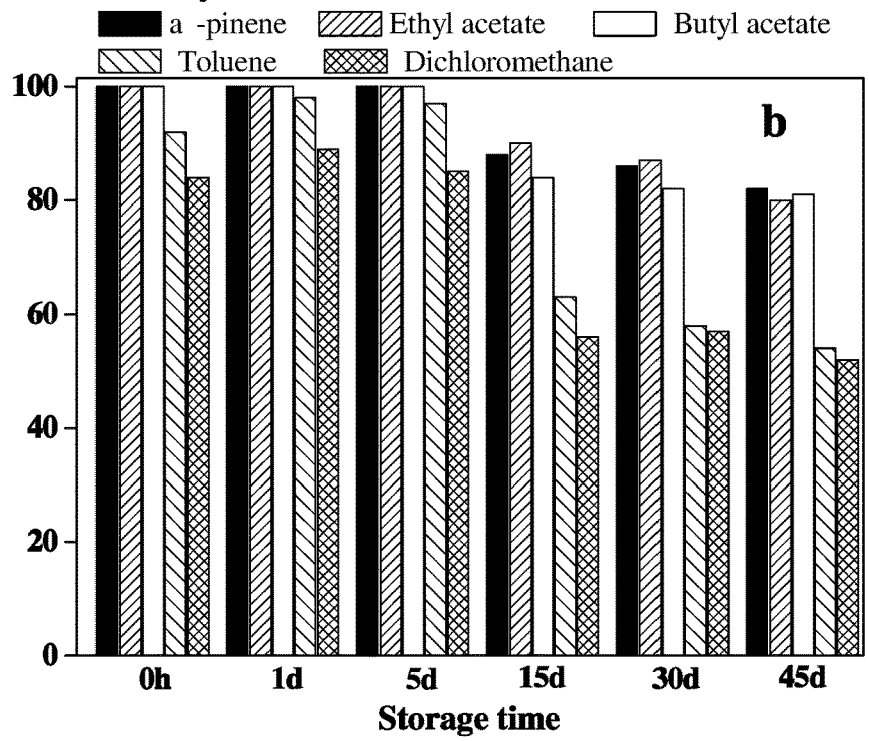
FIG. 2B shows a test result of degradation activity stability of a fungi-bacteria composite microecologics after 72 hrs cultivation according to one embodiment of the invention.

It is known from results shown in FIGS. 2A-2B, after 48 hrs cultivation, a large amount of fungi/bacteria grow in the cultivation solutions that have been stored in the refrigerator for 0 h, 1 d, and 5 d. It is indicated by the degradation activity test that the composite microecologics has certain removal effects on the five pollutants. Removal effects (85% in average) on α-pinene, ethyl acetate, and butyl acetate are relatively good, while the removal effects (approximately 60%) on toluene and dichloromethane are relatively low. The composite microecologics that are stored for a relatively long period do not present too strong of the degradation performance after 48 hrs cultivation, and the removal efficiency of the five pollutants are only between 10% and 20%. After 72 hrs cultivation, the composite microecologics that have been stored for 15 d, 30 d, and 45 d grow in good conditions in the cultivation solution, and the removal efficiency of the five pollutants obviously increases, removal efficiencies of α-pinene, ethyl acetate, and ethyl propionate are higher than 80%, and removal efficiencies of toluene and dichloromethane are higher than 50%. Thus, the constructed fungi-bacteria composite microecologics possesses relatively good degradation activity at low temperature, and the longer period the preservation time is, the longer period it quires to recover the degradation activity thereof.

Example 3 Fungi-Bacteria Composite Microecologics

Fungi-bacteria composite microecologics is added with 1.5 kg of the fungi-bacteria composite microecologics per cubic meter of a filler, and a certain amount of domesticated activated sludge is added to inoculate and initiate a reactor. Meanwhile, the domesticated activated sludge is used as a control group. α-pinene, butyl acetate, ethyl acetate, toluene, and dichloromethane are supplied as waste gas sources, concentrations of the waste gases are controlled at 50 mg/m$^3$, and a retention time thereof is 45 s.

Figure 3:
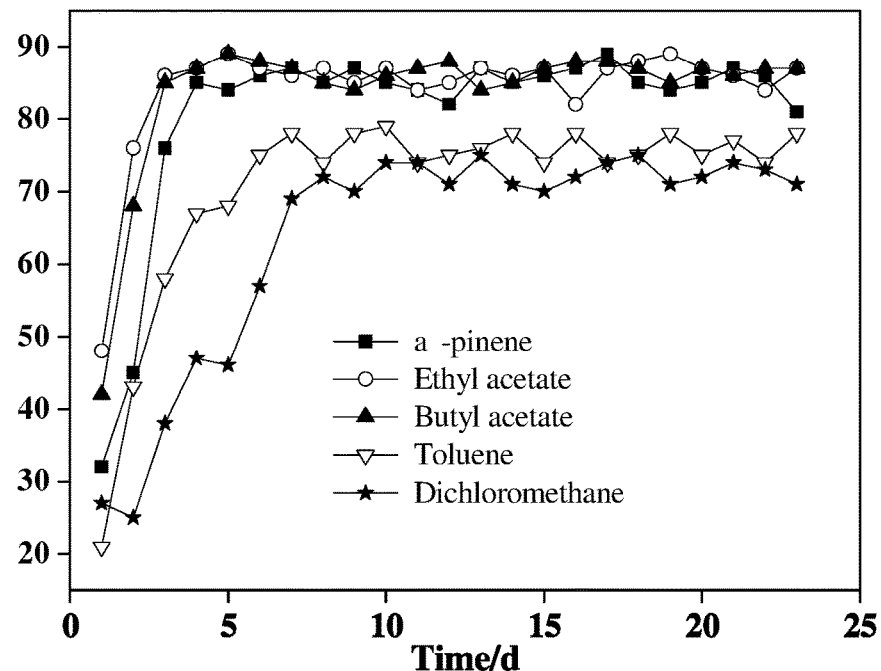
FIG. 3 shows removal efficiencies of different waste gases by waste purification devices initiated by a domesticated activated sludge mixed with a fungi-bacteria composite microecologics.
Figure 4:
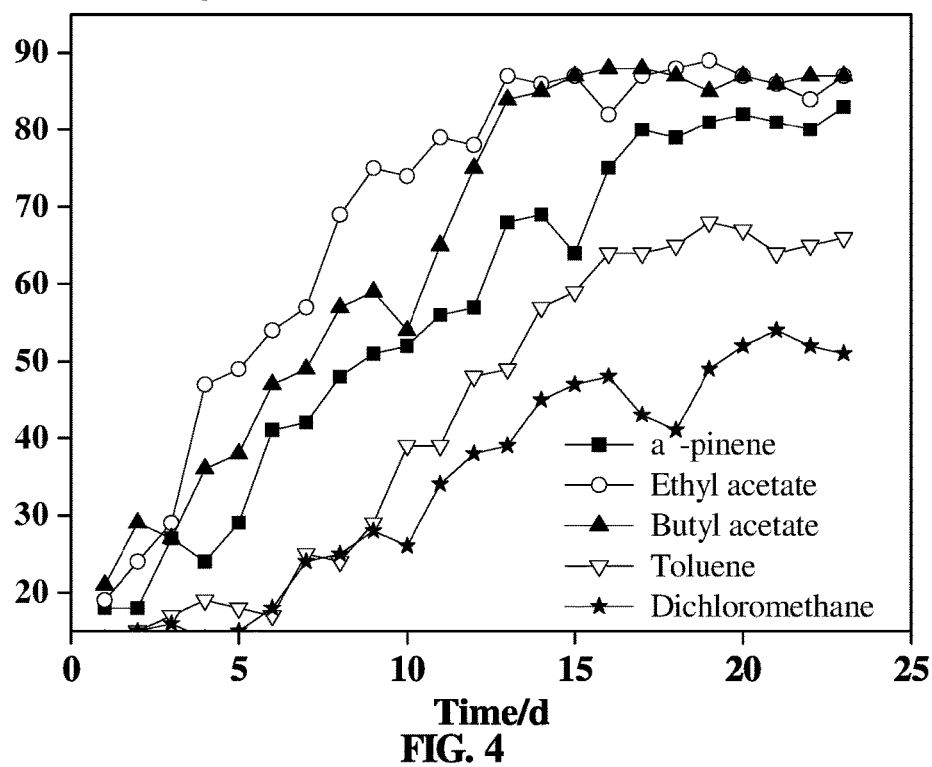
FIG. 4 shows removal efficiencies of different waste gases by waste purification devices initiated only by a domesticated activated sludge.

As illustrated in FIGS. 3-4, it is know that for the reactor initiated by the sludge mixed with the composite microecologics, removal efficiencies of ethyl acetate and butyl acetate after 3 d reach 85% above and remain stable, the removal efficiency of α-pinene after 4 d reaches 85% above and remains stable, the removal efficiency of toluene after 6 d reaches 75% above, and the removal efficiency of dichloromethane reaches 70% above after 8 d and remains stable. Besides, a biofilm is apparently formed on a surface of the filler, which indicates that the biofilm formation is basically successful. For the reactor inoculated only by the activated sludge, the removal efficiencies of pollutants are very slow, and the removal efficiencies of α-pinene, ethyl acetate, butyl acetate, toluene, and dichloromethane after 20 d are maintained at 80%, 85%, 85%, 65%, and 50%, which indicates the biofilm is basically formed. Thus, the bioreactor inoculated with the domesticated activated sludge mixed with the composite microecologics is adapted to obviously shorten the time for biofilm formation, and the removal efficiencies of different pollutants thereof are higher than the reactor inoculated only by activated sludge.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

What is claimed is:

1. A method for preparing a fungi-bacteria composite microecologics, the method comprising:
   1) inoculating a first liquid culture medium using a seed culture tube slant of *Zoogloea resiniphila* strain HJ1 to form activated *Zoogloea resiniphila* strain HJ1 and inoculating a second liquid culture medium using a seed culture tube slant of *Pandoraea pnomenusa* strain FLX-1 to form activated *Pandoraea pnomenusa* strain FLX-1; and conducting high-density fermentation of the activated *Zoogloea resiniphila* strain HJ1 and the activated *Pandoraea pnomenusa* strain FLX-1 respectively in a first fermenter and a second fermenter;
   2) inoculating a potato dextrose agar (PDA) culture medium using a seed culture plate of *Ophiostoma stenoceras* strain LLC to form activated *Ophiostoma stenoceras* strain LLC, and conducting high-density fermentation of the activated *Ophiostoma stenoceras* strain LLC in a third fermenter;
   3) mixing strains obtained from the high-density fermentations of 1) and 2) to form mixed strains, sterilizing a solid-state fermentation (SSF) culture medium, inoculating the SSF culture medium with the mixed strains for solid-state fermentation to form a fermented product, controlling a fermentation temperature at between 30 and 40° C. and a fermentation time for between 24 and 60 hours;
   4) vacuum drying the fermented product obtained from the solid-state fermentation of 3), controlling a drying temperature at 40° C. and a drying time for between 24 and 48 hours; and grinding a resulting product into a powder after drying;
   5) inoculating a first PDA culture medium with a seed culture plate of *Aspergillus fumigatus* strain HD-2 to form activated *Aspergillus fumigatus* strain HD-2 and inoculating a second PDA culture medium with a seed culture plate of *Trichoderma viride* strain LW-1 to form activated *Trichoderma viride* strain LW-1; inoculating a first improved Czapek Dox culture plate with the activated *Aspergillus fumigatus* strain HD-2 and a second improved Czapek Dox culture plate with the activated *Trichoderma viride* strain LW-1, and acquiring a large number of spores respectively from the first improved Czapek Dox culture plate and the second improved Czapek Dox culture plate after between 3 and 5 days of cultivation; and
   6) evenly mixing the powder obtained from 4) and the spores obtained from 5) at a mass ratio of 3-5:1 to form the composite microecologics;
   wherein:
   in 1),
      the first liquid culture medium comprises inorganic salts and the second liquid culture medium comprises inorganic salts;

toluene is a sole carbon source for inoculating the first liquid culture medium using the seed culture tube slant of *Zoogloea resiniphila* strain HJ1;

dichloromethane is a sole carbon source for inoculating the second liquid culture medium using the seed culture tube slant of *Pandoraea pnomenusa* strain FLX-1; and the *Zoogloea resiniphila* strain HJ1 has been deposited in China Center for Type Culture Collection (CCTCC) with an accession number: CCTCC NO. M2012235 and comprises a DNA sequence of SEQ ID NO: 4; and the *Pandoraea pnomenusa* strain FLX-1 has been deposited in CCTCC with an accession number: CCTCC NO. M2011242 and comprises a DNA sequence of SEQ ID NO: 5;

in 2),

α-pinene is a sole carbon source for inoculating the potato dextrose agar (PDA) culture medium using the seed culture plate of *Ophiostoma stenoceras* strain LLC;

α-pinene is a sole carbon source for conducting high-density fermentation of the activated *Ophiostoma stenoceras* strain LLC; and the *Ophiostoma stenoceras* strain LLC has been deposited in CCTCC with an accession number CCTCC NO. M2014531 and comprises a DNA sequence of SEQ ID NO: 3; and in 5), the first improved Czapek Dox culture plate comprises butyl acetate and the second improved Czapek Dox culture plate comprises ethyl acetate; and the *Trichoderma viride* strain LW-1 has been deposited in CCTCC with an accession number: CCTCC NO. M2014176 and comprises a DNA sequence of SEQ ID NO: 1; and the *Aspergillus fumigatus* strain HD-2 has been deposited in CCTCC with an accession number: CCTCC NO. M2014175 and comprises a DNA sequence of SEQ ID NO: 2.

2. The method of claim 1, wherein in 1), the first liquid culture medium comprises: 0.376 g/L of $KH_2PO_4$, 0.456 g/L of $K_2HPO_4$, 0.48 g/L of $(NH_4)_2SO_4$, 0.68 g/L of $NaNO_3$, 0.25 g/L of $Mg(NO_3)_2$, 0.011 g/L of $CaCl_2.2H_2O$, trace elements (0.06 g/L of $MnCl_2.H_2O$, 0.088 g/L of $ZnCl_2$, 0.01 g/L of KI, 0.1 g/L of $NaMoO_4.2H_2O$, and 0.05 g/L of $H_3BO_3$) and a pH value of the first liquid culture medium is between 7.0 and 7.2;

the second liquid culture medium comprises: 0.376 g/L of $KH_2PO_4$, 0.456 g/L of $K_2HPO_4$, 0.48 g/L of $(NH_4)_2SO_4$, 0.68 g/L of $NaNO_3$, 0.25 g/L of $Mg(NO_3)_2$, 0.011 g/L of $CaCl_2.2H_2O$, trace elements (0.06 g/L of $MnCl_2.H_2O$, 0.088 g/L of $ZnCl_2$, 0.01 g/L of KI, 0.1 g/L of $NaMoO_4.2H_2O$, and 0.05 g/L of $H_3BO_3$) and a pH value of the second liquid culture medium is between 7.0 and 7.2;

a first culture medium in the first fermenter comprises: 0.376 g/L of $KH_2PO_4$, 0.456 g/L of $K_2HPO_4$, 0.48 g/L of $(NH_4)_2SO_4$, 0.68 g/L of $NaNO_3$, 0.25 g/L of $Mg(NO_3)_2$, 0.011 g/L of $CaCl_2.2H_2O$, trace elements (0.06 g/L of $MnCl_2.H_2O$, 0.088 g/L of $ZnCl_2$, 0.01 g/L of KI, 0.1 g/L of $NaMoO_4.2H_2O$, and 0.05 g/L of $H_3BO_3$) and a pH value of the first culture medium is between 7.0 and 7.2;

a second culture medium in the second fermenter comprises: 0.376 g/L of $KH_2PO_4$, 0.456 g/L of $K_2HPO_4$, 0.48 g/L of $(NH_4)_2SO_4$, 0.68 g/L of $NaNO_3$, 0.25 g/L of $Mg(NO_3)_2$, 0.011 g/L of $CaCl_2.2H_2O$, trace elements (0.06 g/L of $MnCl_2.H_2O$, 0.088 g/L of $ZnCl_2$, 0.01 g/L of KI, 0.1 g/L of $NaMoO_4.2H_2O$, and 0.05 g/L of $H_3BO_3$) and a pH value of the second culture medium is between 7.0 and 7.2;

the first liquid culture medium, the second liquid culture medium, the first culture medium in the first fermenter, and the second culture medium in the second fermenter are performed with moist heat sterilization at a temperature of 121° C. for between 30 and 40 minutes;

toluene is a sole carbon source for conducting high-density fermentation of the activated *Zoogloea resiniphila* strain HJ1;

dichloromethane is a sole carbon source for conducting high-density fermentation of the activated *Pandoraea pnomenusa* strain FLX-1; and temperatures for the activation and the high-density fermentation are controlled at between 30 and 35° C. and dissolved oxygen contents are controlled at between 2 and 3 mg/L.

3. The method of claim 1, wherein in 2), the PDA culture medium comprises: 200 g/L of potato, 20 g/L of glucose (or sucrose), and 20 g/L of agar, and a pH value of the PDA culture medium is 6.5;

a third culture medium in the third fermenter comprises: 2.0 g/L of $NH_4Cl$, 0.47 g/L of $Na_2HPO_4$, 0.45 g/L of $KH_2PO_4$, 0.5 g/L of $MgSO_4$, 0.01 g/L of anhydrous $CaCl_2$, and trace elements (0.001 g/L of $Mn^{2+}$, $Fe^{2+}$, $Cu^{2+}$, and $Zn^{2+}$, respectively), a pH value of the third culture medium in the third fermenter is between 4.2 and 4.6, and a carbon source of the third culture medium in the third fermenter is α-pinene;

both the PDA culture medium and the third culture medium of the third fermenter are performed with moist heat sterilization at a temperature of 121° C. for between 30 and 40 minutes;

the activation and the high-density fermentation of the *Ophiostoma stenoceras* strain LLC are conducted at temperatures of between 30 and 35° C.; and a dissolved oxygen concentration during the high-density fermentation is controlled at between 2 and 3 mg/L.

4. The method of claim 1, wherein in 3), the SSF culture medium comprises a solid state composite comprising wheat bran accounting for between 45 and 50 wt. % of the total weight of the solid state composite, sawdust accounting for between 25 and 30 wt. % of the total weight of the solid state composite, and powdered activated carbon accounting for between 25 and 30 wt. % of the total weight of the solid state composite;

an aqueous solution having a volume of between 1 and 2 times of that of the solid state composite is added to the solid state composite to yield a mixture;

the aqueous solution comprises: 20 g/L of a yeast extract, 20 g/L of potato, and 5 g/L of NaCl;

a pH value of the mixture is regulated to be between 6.8 and 7.2; and the mixture is conducted with moist heat sterilization at a temperature of 121° C. for between 30 and 40 minutes and then cooled to obtain the SSF culture medium.

5. The method of claim 1, wherein in 3), an inoculum concentration of the mixed strains in the SSF culture medium is between 5 and 20%.

6. The method of claim 1, wherein in 5), the first improved Czapek Dox culture plate and the second improved Czapek Dox culture plate comprise: 3 g/L of $NaNO_3$, 0.5 g/L of $MgSO_4$, 0.5 g/L of KCl, 0.01 g/L of $FeSO_4$, and 20 g of agar, and pH values of the first improved Czapek Dox culture plate and the second improved Czapek Dox culture plat are between 6.0 and 6.5;

the butyl acetate and the ethyl acetate are supplied as carbon sources for the activated *Aspergillus fumigatus* strain HD-2 and the activated *Trichoderma viride* strain LW-1, respectively; and the first improved Czapek Dox culture plate and the second improved Czapek Dox culture plate are conducted with moist heat sterilization at a temperature of 121° C. for between 30 and 40 minutes.

7. The method of claim 1, wherein the composite microecologics obtained from 6) is in a solid powder state and is adapted to maintain viabilities thereof after preservation at room temperature or a temperature of 4° C. for more than 45 days.

\* \* \* \* \*